US011122985B2

(12) United States Patent
Sato et al.

(10) Patent No.: US 11,122,985 B2
(45) Date of Patent: Sep. 21, 2021

(54) BIOPOTENTIAL MEASURING APPARATUS

(71) Applicant: NIHON KOHDEN CORPORATION, Tokyo (JP)

(72) Inventors: Makoto Sato, Tokyo (JP); Toshiki Maeda, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 340 days.

(21) Appl. No.: 16/308,311

(22) PCT Filed: May 12, 2017

(86) PCT No.: PCT/JP2017/018075
§ 371 (c)(1),
(2) Date: Dec. 7, 2018

(87) PCT Pub. No.: WO2017/217158
PCT Pub. Date: Dec. 21, 2017

(65) Prior Publication Data
US 2019/0183376 A1   Jun. 20, 2019

(30) Foreign Application Priority Data
Jun. 16, 2016 (JP) .............................. JP2016-120196

(51) Int. Cl.
*A61B 5/053* (2021.01)
*A61N 1/37* (2006.01)
(Continued)

(52) U.S. Cl.
CPC .............. *A61B 5/053* (2013.01); *A61B 5/377* (2021.01); *A61B 5/7203* (2013.01); *A61B 5/725* (2013.01);
(Continued)

(58) Field of Classification Search
CPC .......... A61N 1/371–3716; A61B 5/053; A61B 5/24; A61B 5/7203–7207; A61B 5/7225; A61B 2562/0214
See application file for complete search history.

(56) References Cited

U.S. PATENT DOCUMENTS 5,018,523 A   5/1991  Bach, Jr. et al.
5,941,903 A   8/1999  Zhu et al.
(Continued)

FOREIGN PATENT DOCUMENTS

| JP | S48-065786 A | 9/1973 |
| JP | S51-094893 A | 8/1976 |
| JP | H01-178004 U | 12/1989 |

OTHER PUBLICATIONS

International Search Report Issued in Patent Application No. PCT/JP2017/018075 dated Aug. 18, 2017.
(Continued)

*Primary Examiner* — Thaddeus B Cox
(74) *Attorney, Agent, or Firm* — Pearne & Gordon LLP (57) ABSTRACT

A stimulating section applies stimulation to a living body. A first lead electrode and a second lead electrode are attached on the living body. A first amplifier circuit amplifies potential difference that is evoked between the first lead electrode and the second lead electrode due to the stimulation. A first switch cancels electrical connection between the first amplifier circuit and each of the first lead electrode and the second lead electrode at least while the stimulation is applied. A high-pass filter includes a capacitor (C) and filters a frequency component of an output from the first amplifier circuit that is no less than a predetermined value. A second amplifier circuit amplifies the output from the first amplifier circuit. A second switch stops charging/discharging of the capacitor (C) and decreases a gain of the second amplifier
(Continued)

circuit at least while the first switch cancels the electrical connection.

10 Claims, 3 Drawing Sheets

(51) Int. Cl.
    *A61B 5/377*     (2021.01)
    *A61B 5/24*     (2021.01)
    *A61B 5/304*     (2021.01)
    *A61B 5/00*     (2006.01)
    *A61B 5/30*     (2021.01)

(52) U.S. Cl.
    CPC .......... *A61B 5/7217* (2013.01); *A61B 5/7225* (2013.01); *A61N 1/371* (2013.01); *A61B 5/24* (2021.01); *A61B 5/30* (2021.01); *A61B 5/304* (2021.01); *A61B 2560/0468* (2013.01); *A61B 2562/0214* (2013.01)

(56) References Cited

U.S. PATENT DOCUMENTS

| | | |
|---|---|---|
| 6,473,649 B1 | 10/2002 | Gryzwa et al. |
| 7,424,322 B2 | 9/2008 | Lombardi et al. |
| 2004/0167577 A1* | 8/2004 | Legay .................... A61N 1/371 607/4 |
| 2006/0173496 A1* | 8/2006 | Lombardi .......... A61B 5/04001 607/2 |

OTHER PUBLICATIONS

Written Opinion Issued in Patent Application No. PCT/JP2017/018075 dated Aug. 18, 2017.
Bergmann, Til O., et al., "EEG-Guided Transcranial Magnetic Stimulation Reveals Rapid Shifts in Motor Cortical Excitability during the Human Sleep Slow Oscillation", Journal of Neuroscience, Jan. 4, 2012, 32(1), pp. 243-253.
McGill, Kevin C., et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Japanese Office action issued in Japanese Patent Application No. 2016-120196 dated Apr. 7, 2020.

* cited by examiner

BIOPOTENTIAL MEASURING APPARATUS

TECHNICAL FIELD

The present invention relates to a biopotential measuring apparatus, and particularly to an apparatus (so-called evoked potential measuring apparatus) for measuring a potential difference which appears between lead electrodes as a response evoked in a living body by stimulation.

BACKGROUND ART

As an examination in which a response of muscle or nerve is evoked by stimulation from the outside, known are motor-evoked potentials (MEPs), somatosensory-evoked potentials (SEPs), nerve conduction studies (NCSs), and the like. In such an examination, a pair of lead electrodes is attached to a living body. Magnetic stimulation or electric stimulation is used as stimulation for evoking a response. A response evoked by stimulation is recorded in the form of a response waveform which corresponds to a temporal change of the potential difference appearing between the pair of lead electrodes. The time period (latency) from application of stimulation to appearance of the response waveform, or the amplitude of the response waveform is used as an examination index.

Figure 3A:
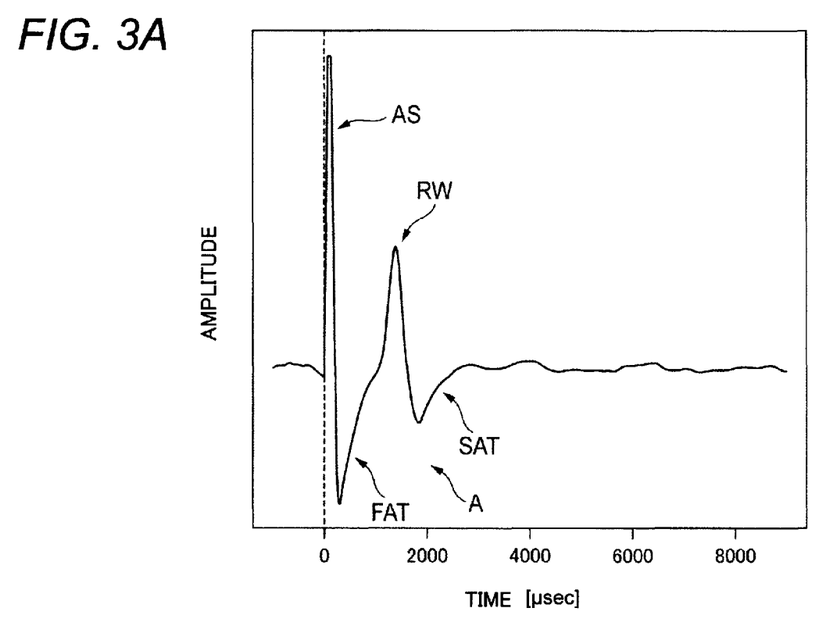
FIG. 3A illustrates an evoked potential acquired by a conventional evoked potential measuring apparatus.

FIG. 3A illustrates an example of the temporal change of the evoked potential difference appearing between the lead electrodes. The abscissa indicates the time, and the ordinate indicates the amplitude. The zero in the abscissa shows the time point of application of stimulation. The reference numeral RW denotes a response waveform which is evoked by the stimulation. As seen from the figure, a stimulation artifact A which is synchronized with the time point of stimulation is overlapped with the evoked potential.

According to Non-patent Document 1, a stimulation artifact A due to electric stimulation is classified into three components or an artifact spike AS, a fast artifact tail FAT, and a slow artifact tail SAT. The fast artifact tail FAT and the slow artifact tail SAT are sustained for a while even after application of stimulation is terminated. The same applies to a stimulation artifact due to magnetic stimulation (Non-patent Document 2). According to these Documents, artifact tails have a property that they are sustained for several milliseconds to several tens of milliseconds.

CITATION LIST

Non Patent Literature

NPL 1: McGill K C, Cummins K L, Dorfman L J, Berlizot B B, Leutkemeyer K, Nishimura D G, Widrow B. On the Nature and Elimination of Stimulus Artifact in Nerve Signals Evoked and Recorded Using Surface Electrodes. IEEE Trans Biomed Eng. 1982 February; 29(2):129-37.
NPL 2: Bergmann T O, Molle M, Schmidt M A, Lindner C, Marshall L, Born J, Siebner H R. EEG-Guided Transcranial Magnetic Stimulation Reveals Rapid Shifts in Motor Cortical Excitability during the Human Sleep Slow Oscillation. J Neurosci. 2012 Jan. 4; 32(1):243-53.

SUMMARY OF INVENTION

Technical Problem

When the duration of the artifact tail components is prolonged, the response waveform RW and the stimulation artifact SA happen to overlap with each other, so that the response waveform RW is distorted. In such a case, it is difficult to correctly measure the latency and amplitude of the response waveform, so that the examination would be adversely affected.

It is thus demanded to suppress a stimulation artifact to improve the accuracy of measurement of a biopotential.

Solution to Problem

One aspect for meeting the above demand is a biopotential measuring apparatus comprising:
a stimulating section configured to apply stimulation to a living body;
a first lead electrode adapted to be attached on the living body;
a second lead electrode adapted to be attached on the living body;
a first amplifier circuit configured to amplify potential difference that is evoked between the first lead electrode and the second lead electrode due to the stimulation;
a first switch configured to cancel electrical connection between the first amplifier circuit and each of the first lead electrode and the second lead electrode at least while the stimulation is applied;
a high-pass filter including a capacitor and configured to filter a frequency component of an output from the first amplifier circuit that is no less than a predetermined value;
a second amplifier circuit configured to amplify the output from the first amplifier circuit; and
a second switch configured to stop charging/discharging of the capacitor and to decrease a gain of the second amplifier circuit at least while the first switch cancels the electrical connection between the first amplifier circuit and each of the first lead electrode and the second lead electrode.

When currents flow from the first and second lead electrodes into the first amplifier circuit at the time of the stimulation, a potential difference is generated between the living body and the ground potential of the first amplifier circuit, which causes a fast artifact tail. According to the above-described operation, however, the first and second lead electrodes are opened at least while the stimulation is applied. Accordingly, it is possible to suppress currents flowing into the first and second lead electrodes. As a result, a fast artifact tail which is to be overlapped with the evoked potential can be suppressed, so that the accuracy of measurement of the biopotential can be improved.

When the first switch is opened or closed, and while the first and second lead electrodes are opened by the first switch, noises may easily enter the first amplifier circuit. In this case, the noises are amplified by the subsequent second amplifier circuit. In the above-described operation, however, the gain of the second amplifier circuit is decreased at least while the electrical connections between the first and second lead electrodes and the first amplifier circuit are canceled. Therefore, noises which are to be overlapped with the evoked potential can be suppressed, so that the accuracy of measurement of the biopotential can be improved.

The time period in which the stimulation is applied to the living body is contained in the time period in which the electrical connections between the first and second lead electrodes and the first amplifier circuit are canceled. That is, the gain of the second amplifier circuit is decreased while the stimulation is applied by the stimulating section. Therefore, the evoked potential which is acquired during the application of stimulation can be suppressed. Consequently, an artifact spike which is generated almost concurrently with the stimulation can be prevented from being overlapped with the evoked potential, so that the accuracy of measurement of the biopotential can be improved.

The charging/discharging of the capacitor cause a slow artifact tail to be overlapped with the evoked potential. According to the above-described operation, however, the operations of charging/discharging the capacitor are stopped at least while the stimulation is applied by the stimulating section. Therefore, a slow artifact tail which is to be overlapped with the evoked potential can be suppressed, so that the accuracy of measurement of the biopotential can be improved.

One aspect for meeting the above demand is a biopotential measuring apparatus comprising:

a stimulating section configured to apply stimulation to a living body;

a first lead electrode adapted to be attached on the living body;

a second lead electrode adapted to be attached on the living body;

an amplifier circuit configured to amplify potential difference that is evoked between the first lead electrode and the second lead electrode due to the stimulation; and a switch configured to cancel electrical connection between the amplifier circuit and each of the first lead electrode and the second lead electrode at least while the stimulation is applied.

With this configuration, the first and second lead electrodes are opened at least while the stimulation is applied. Accordingly, it is possible to suppress currents flowing into the first and second lead electrodes. As a result, a fast artifact tail which is to be overlapped with the evoked potential can be suppressed, so that the accuracy of measurement of the biopotential can be improved.

One aspect for meeting the above demand is a biopotential measuring apparatus comprising:

a stimulating section configured to apply stimulation to a living body;

a first lead electrode adapted to be attached on the living body;

a second lead electrode adapted to be attached on the living body;

an amplifier circuit configured to amplify potential difference that is evoked between the first lead electrode and the second lead electrode due to the stimulation;

a high-pass filter including a capacitor and configured to filter a frequency component of an output from the amplifier circuit that is no less than a predetermined value; and a switch configured to stop charging/discharging of the capacitor at least while the stimulation is applied.

With this configuration, the operations of charging/discharging the capacitor C are stopped at least while the stimulation is applied by the stimulating section. Therefore, a slow artifact tail which is to be overlapped with the evoked potential can be suppressed, so that the accuracy of measurement of the biopotential can be improved.

One aspect for meeting the above demand is a biopotential measuring apparatus comprising:

a stimulating section configured to apply stimulation to a living body;

a first lead electrode adapted to be attached on the living body;

a second lead electrode adapted to be attached on the living body;

a first amplifier circuit configured to amplify potential difference that is evoked between the first lead electrode and the second lead electrode due to the stimulation;

a first switch configured to cancel electrical connection between the first amplifier circuit and each of the first lead electrode and the second lead electrode at least while the stimulation is applied;

a second amplifier circuit configured to amplify an output from the first amplifier circuit; and a second switch configured to decrease a gain of the second amplifier circuit at least while the first switch cancels the electrical connection between the first amplifier circuit and each of the first lead electrode and the second lead electrode.

With this configuration, the gain of the second amplifier circuit is decreased at least while the electrical connections between the first and second lead electrodes and the first amplifier circuit are canceled. Therefore, noises which are to be overlapped with the evoked potential can be suppressed, so that the accuracy of measurement of the biopotential can be improved.

One aspect for meeting the above demand is a biopotential measuring apparatus comprising:

a stimulating section configured to apply stimulation to a living body;

a first lead electrode adapted to be attached on the living body;

a second lead electrode adapted to be attached on the living body;

an amplifier circuit configured to amplify potential difference that is evoked between the first lead electrode and the second lead electrode due to the stimulation;

a high-pass filter configured to filter a frequency component of an output from the amplifier circuit that is no less than a predetermined value; and a switch configured to stop increase a cutoff frequency of the high-pass filter after the stimulation is applied.

In each of the first and second lead electrodes, polarization occurs in accordance with the stimulation. The polarization voltage consists of a DC component. Until the recorded waveform is returned to the baseline potential by the high-pass filter, the DC component is overlapped with the evoked potential as a stimulation artifact. The shorter the time constant of the high-pass filter, the sooner the DC component returns to the baseline potential. With the above configuration, it is possible to suppress the stimulation artifact which is to be overlapped with the evoked potential due to the polarization voltage, so that the accuracy of measurement of the biopotential can be improved.

DESCRIPTION OF EMBODIMENTS

Figure 1:
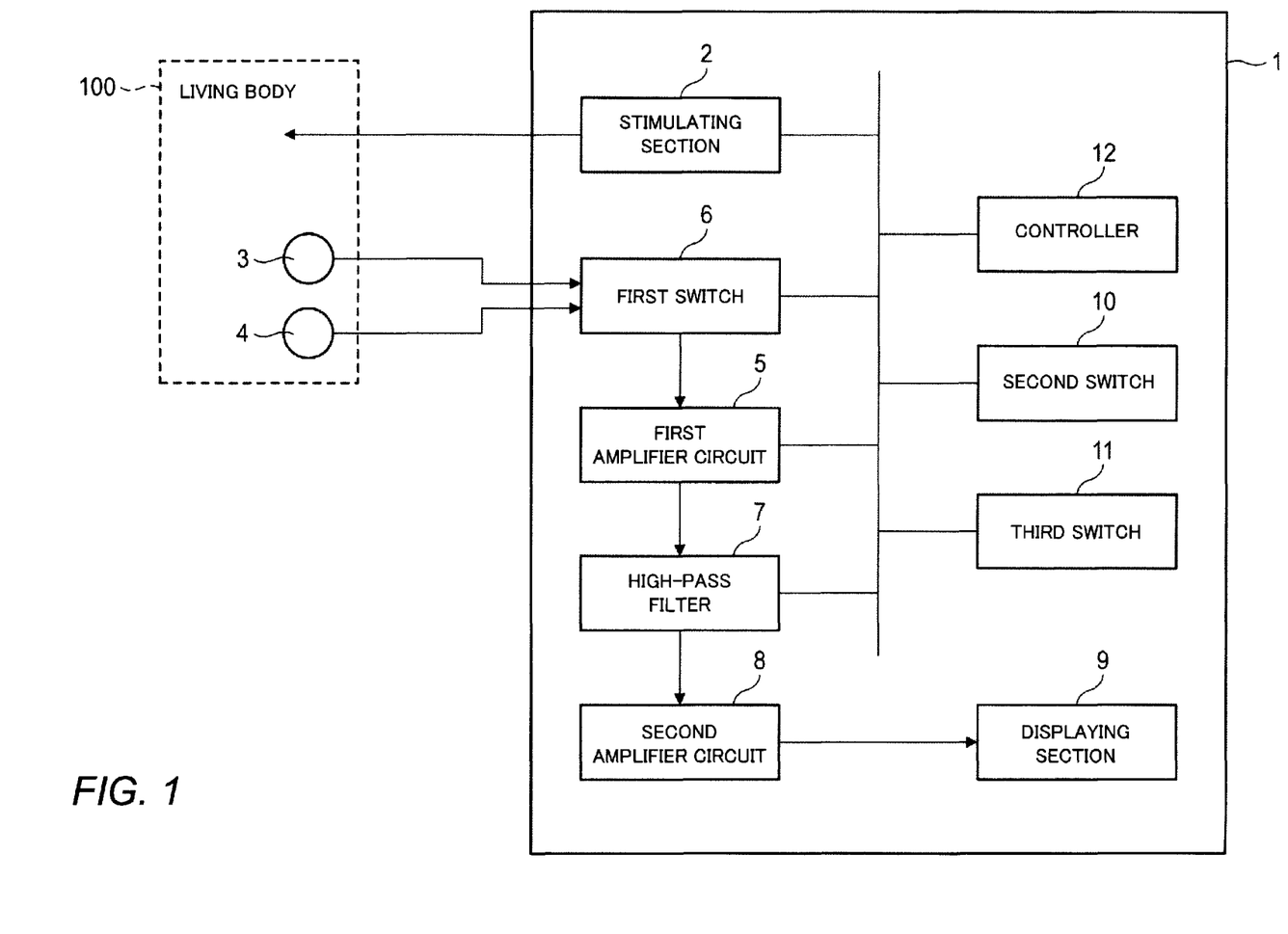
FIG. 1 illustrates a functional configuration of an evoked potential measuring apparatus according to one embodiment.

An embodiment will be described in detail with reference to the accompanying drawings. FIG. 1 shows the functional configuration of an evoked potential measuring apparatus 1 (an example of the biopotential measuring apparatus) of the embodiment.

The evoked potential measuring apparatus 1 comprises a stimulating section 2. The stimulating section 2 is configured to apply stimulation to a living body 100. Electric stimulation and magnetic stimulation may be exemplified as such stimulation.

The evoked potential measuring apparatus 1 further comprises a first lead electrode 3 and a second lead electrode 4. The first and second lead electrodes 3, 4 are configured to be attached to adequate places on the living body 100. In accordance with stimulation by the stimulating section 2, a potential difference is evoked between the first and second lead electrodes 3, 4.

The evoked potential measuring apparatus 1 further comprises a first amplifier circuit 5 and a first switch 6. The first switch 6 is configured to selectively establish or cancel an electrical connection between the first lead electrode 3 and the first amplifier circuit 5, as well as between the second lead electrode 4 and the first amplifier circuit 5. The first amplifier circuit 5 is configured to, while the first and second lead electrodes 3, 4 are electrically connected to the first amplifier circuit 5, amplify the potential difference which is produced between the first and second lead electrodes 3, 4.

The evoked potential measuring apparatus 1 further comprises a high-pass filter 7. The high-pass filter 7 is electrically connected to the first amplifier circuit 5. The high-pass filter 7 is configured to filter a frequency component of an output from the first amplifier circuit 5 that is no less than a predetermined value.

The evoked potential measuring apparatus 1 further comprises a second amplifier circuit 8. The second amplifier circuit 8 is electrically connected to the high-pass filter 7. The second amplifier circuit 8 is configured to amplify the output of the first amplifier circuit 5 which has passed through the high-pass filter 7.

The evoked potential measuring apparatus 1 further comprises a displaying section 9. The displaying section 9 is electrically connected to the second amplifier circuit 8. The displaying section 9 is configured to convert the output of the second amplifier circuit 8 into a mode which can be viewed by the user, and to display the converted output. A waveform, a numerical value, a text, and a symbol may be exemplified as such a mode.

The evoked potential measuring apparatus 1 further comprises a second switch 10. The second switch 10 is electrically connected to the high-pass filter 7 and the second amplifier circuit 8.

The evoked potential measuring apparatus 1 further comprises a third switch 11. The third switch 11 is electrically connected to the high-pass filter 7.

The evoked potential measuring apparatus 1 further comprises a controller 12. The controller 12 is configured to supply control signals to the stimulating section 2, the first switch 6, the second switch 10, and the third switch 11, respectively.

Figure 2A:
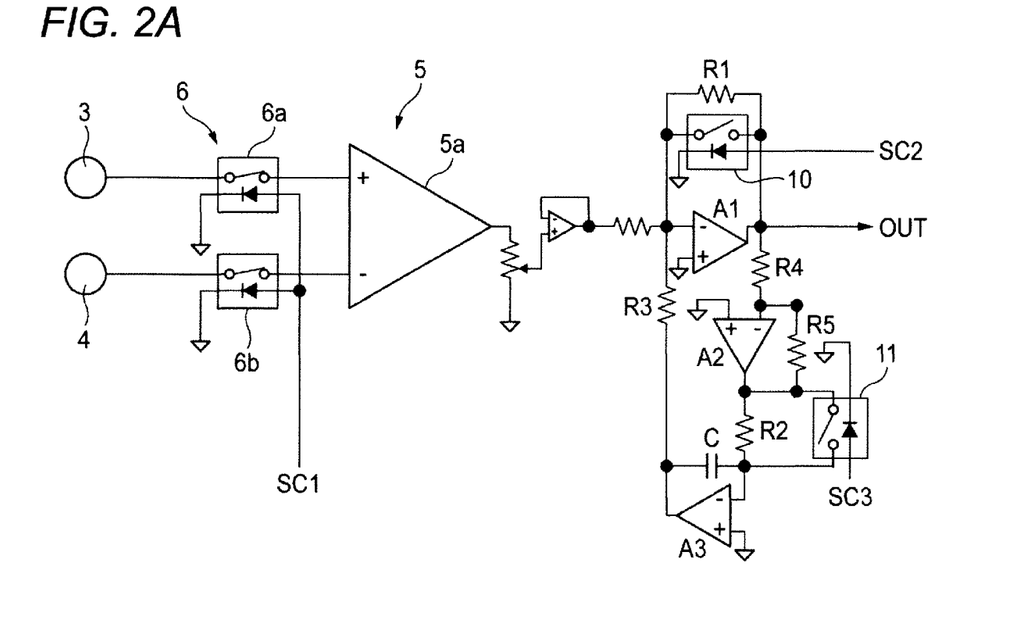
FIG. 2A illustrates a circuit configuration of a part of the evoked potential measuring apparatus of FIG. 1.

FIG. 2A illustrates a specific example of the circuit configuration of a part of the thus configured evoked potential measuring apparatus 1.

The first amplifier circuit 5 includes a differential amplifier 5a. The first switch 6 includes a switch element 6a and a switch element 6b. The switch element 6a is electrically connected to the first lead electrode 3 and a non-inverting input terminal of the differential amplifier 5a. The switch element 6a is configured to selectively establish or cancel the electrical connection between them. The switch element 6b is electrically connected to the second lead electrode 4 and the inverting input terminal of the differential amplifier 5a. The switch element 6b is configured to selectively establish or cancel the electrical connection between them.

The controller 12 is configured to output a control signal SC1 for opening and closing the switch elements 6a, 6b of the first switch 6.

The output of the differential amplifier 5a is supplied to a subsequent circuit via a variable resistor (for signal attenuation) and a buffer amplifier (for impedance conversion). This circuit includes amplifiers A1 to A3, resistors R1 to R5, and a capacitor C. This circuit serves as both of the high-pass filter 7 and the second amplifier circuit 8 (the inverting amplifier circuit).

When the gain of the second amplifier circuit 8 is represented by G, the cutoff frequency $f_c$ and offset voltage $V_{of}$ of the high-pass filter 7 are expressed by the following expressions:

$$f_c = (1/2p) \times (G/R_2 C)$$

$$V_{of} = -(R_4/R_5) \times (R_2 I_B) - V_{OS} \times (R_4/R_5)$$

where $R_2$ represents the resistance of the resistor R2; $R_4$ represents the resistance of the resistor R4; $R_5$ represents the resistance of the resistor R5; C represents the capacitance of the capacitor C; $I_B$ represents the input bias current of the amplifier A3; and $V_{OS}$ represents the input offset voltage of the amplifier A3. Since the relationships between the parameters of the circuit elements and the behavior of the circuit are clearly known, the frequency and the voltage can be easily adjusted in accordance with the required specifications.

The output of the amplifier A1 is converted into an adequate mode via appropriate circuits such as an A/D converter. The converted output is then supplied to the displaying section 9.

The second switch 10 is connected in parallel to the both terminals of the resistor R1. The controller 12 is configured to output a control signal SC2 for opening and closing the second switch 10.

The third switch 11 is connected in parallel to the both terminals of the resistor R2. The controller 12 is configured to output a control signal SC3 for opening and closing the third switch 11.

Figure 2B:
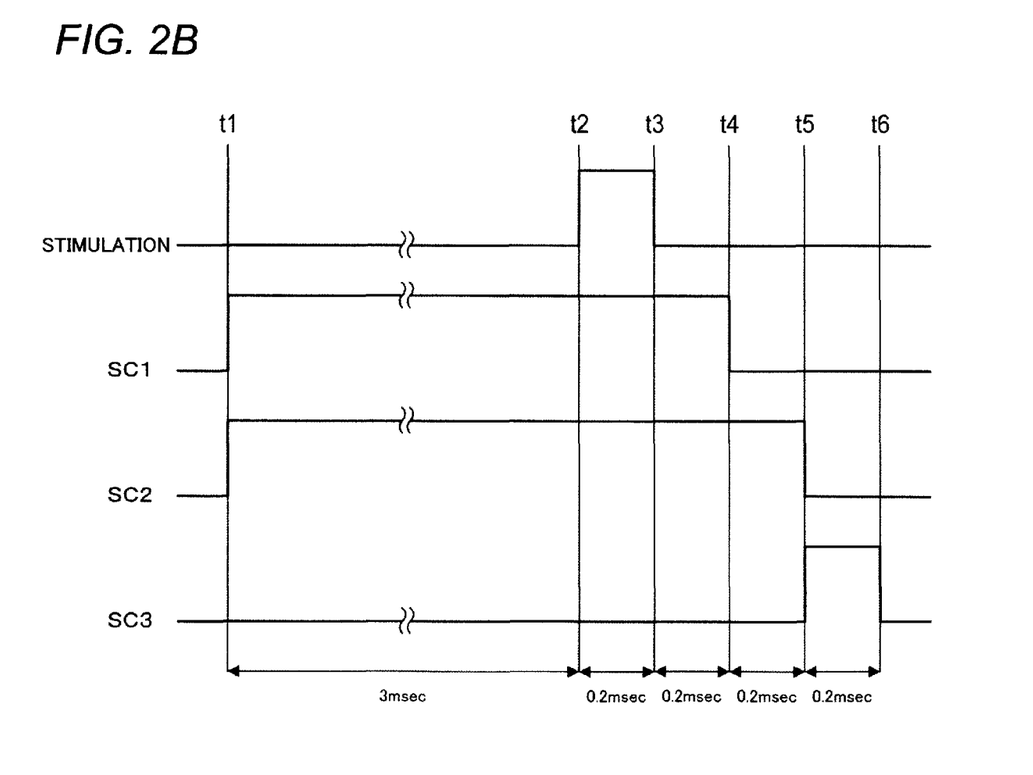
FIG. 2B illustrates operations of the evoked potential measuring apparatus of FIG. 1.

FIG. 2B is a time point chart illustrating the operation of the thus configured evoked potential measuring apparatus 1. The time values illustrated in this figure are mere examples.

The controller 12 supplies the control signal to the stimulating section 2 to cause stimulation to be applied to the living body 100. The controller 12 supplies the control signal SC1 to the first switch 6, thereby causing the first switch 6 to, at least while the stimulation is applied (time period t2 to t3), cancel the electrical connections between the first and second lead electrodes 3, 4 and the first amplifier circuit 5 (time period t1 to t4). The time point t1 is adequately determined in consideration of the delay of the first switch 6 in response to the control signal SC1.

In the example illustrated in FIG. 2A, the switch element 6a is opened by the control signal SC1, so that the electrical connection between the first lead electrode 3 and the non-inverting input terminal of the differential amplifier 5a is canceled. Similarly, the switch element 6b is opened by the control signal SC1, so that the electrical connection between the second lead electrode 4 and the inverting input terminal of the differential amplifier 5a is canceled.

When currents flow from the first and second lead electrodes 3, 4 into the first amplifier circuit 5 in accordance with the stimulation, a potential difference is generated between the living body 100 and the ground potential of the first amplifier circuit 5, which causes a fast artifact tail. According to the above-described operation, however, the first and second lead electrodes 3, 4 are opened at least while the stimulation is applied. Accordingly, it is possible to suppress currents flowing into the first and second lead electrodes 3, 4. As a result, a fast artifact tail which is to be overlapped with the evoked potential can be suppressed, so that the accuracy of measurement of the evoked potential (an example of the biopotential) can be improved. This effect is remarkable particularly in the case where the stimulating section 2 applies electric stimulation to the living body 100 through stimulation electrodes.

On the other hand, as illustrated in FIG. 2B, the controller 12 supplies the control signal SC2 to the second switch 10, thereby causing the second switch 10 to decrease the gain G of the second amplifier circuit 8 (time period t1 to t5), at least while the electrical connections between the first and second lead electrodes 3, 4 and the first amplifier circuit 5 is canceled by the first switch 6 (time period t1 to t4).

The time point t1 is adequately determined in consideration of the delay of the second switch 10 in response to the control signal SC2. Although, in the example illustrated in FIG. 2B, the first and second switches 6, 10 are simultaneously operated, the second switch 10 may be operated prior to the operation of the first switch 6.

In the example illustrated in FIG. 2A, the second switch 10 is closed in response to the control signal SC2, so that the gain of the amplifier A1 constituting a part of the second amplifier circuit 8 is set to substantially zero.

When the first switch 6 is opened or closed, and while the first and second lead electrodes 3, 4 are opened by the first switch 6, noises may easily enter the first amplifier circuit 5. In this case, the noises are amplified by the subsequent second amplifier circuit 8. In the above-described operation, however, the gain G of the second amplifier circuit 8 is decreased at least while the electrical connections between the first and second lead electrodes 3, 4 and the first amplifier circuit 5 are canceled. Therefore, noises which are to be overlapped with the evoked potential can be suppressed, so that the accuracy of measurement of the evoked potential can be improved.

As described above, the time period (t2 to t3) in which the stimulation is applied to the living body 100 is contained in the time period (t1 to t4) in which the electrical connections between the first and second lead electrodes 3, 4 and the first amplifier circuit 5 are canceled. That is, the gain G of the second amplifier circuit 8 is decreased while the stimulation is applied by the stimulating section 2. Therefore, the evoked potential which is acquired during the application of stimulation can be suppressed. Consequently, an artifact spike which is generated almost concurrently with the stimulation can be prevented from being overlapped with the evoked potential, so that the accuracy of measurement of the evoked potential can be improved.

Moreover, the control signal SC2 supplied to the second switch 10 causes the second switch 10 to stop the charging/discharging of the capacitor C of the high-pass filter 7 during the time period t1 to t5 but at least while the electrical connections between the first and second lead electrodes 3, 4 and the first amplifier circuit 5 are canceled by the first switch 6 (time period t1 to t4).

In the example illustrated in FIG. 2A, when the second switch 10 is closed by the control signal SC2, the voltage of the output terminal of the amplifier A2 is decreased to zero, whereby the charging/discharging operations of the capacitor C are stopped.

The charging/discharging of the capacitor C cause a slow artifact tail to be overlapped with the evoked potential. According to the above-described operation, however, the operations of charging/discharging the capacitor C are stopped at least while the stimulation is applied by the stimulating section 2. Therefore, a slow artifact tail which is to be overlapped with the evoked potential can be suppressed, so that the accuracy of measurement of the evoked potential can be improved.

As illustrated in FIG. 2B, the controller 12 supplies the control signal SC3 to the third switch 11, thereby causing the third switch 11 to, after stimulation is applied by the stimulating section 2 to the living body 100, raise the cutoff frequency $f_c$ of the high-pass filter 7.

In the example illustrated in FIG. 2A, the third switch 11 is closed in response to the control signal SC3, so that the time constant of the high-pass filter 7 is decreased. Therefore, the cutoff frequency $f_c$ of the high-pass filter 7 is raised.

In each of the first and second lead electrodes 3, 4, polarization occurs in association with the stimulation from the stimulating section 2. The polarization voltage consists of a DC component. Until the input waveform is returned to the baseline potential by the high-pass filter 7, the DC component is overlapped with the evoked potential as a stimulation artifact. The shorter the time constant of the high-pass filter, the sooner the DC component returns to the baseline potential. According to such an operation, it is possible to suppress the stimulation artifact which is to be overlapped with the evoked potential due to the polarization voltage, so that the accuracy of measurement of the evoked potential can be improved. Particularly in the case where magnetic stimulation is applied by the stimulating section 2, the polarization voltage is very high, so that the above-described effect due to suppression of a stimulation artifact is remarkable.

Figure 3B:
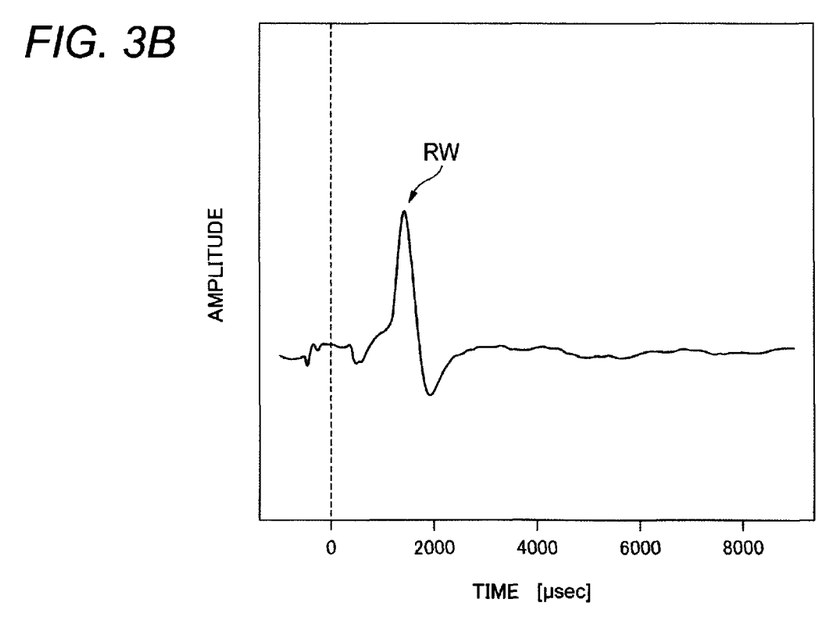
FIG. 3B illustrates an evoked potential acquired by the evoked potential measuring apparatus of FIG. 1.

FIG. 3B illustrates an example of an evoked potential which is acquired in the case where the first, second, and third switches 6, 10, 11 operate as described above. As compared with the waveform illustrated in FIG. 3A, it can be seen that an artifact spike AS is not generated, as well as overlapping of a fast artifact tail FAT and a slow artifact tail SAT are suppressed. Therefore, a response waveform RW which is evoked by stimulation can be clearly seen, and the latency and amplitude of the response waveform RW which are necessary in an examination can be correctly measured.

More specifically, as illustrated in FIG. 2B, the controller 12 causes at time point t4 the first switch 6 to recover the electrical connections between the first and second lead electrodes 3, 4 and the first amplifier circuit 5, and then causes the third switch 11 by means of the control signal SC3 to raise the cutoff frequency $f_c$ of the high-pass filter 7.

When the second switch 10 cancels the stopping of the charging/discharging of the capacitor C and the decreasing of the gain of the second amplifier circuit 8 at the time point t5 or later, the controller 12 causes the third switch 11 by means of the control signal SC3 to raise the cutoff frequency $f_c$ of the high-pass filter 7.

Furthermore, before the response waveform RW evoked by stimulation appears between the first and second lead electrodes 3, 4, the controller 12 causes the third switch 11 by means of the control signal SC3 to restore the cutoff frequency $f_c$ of the high-pass filter 7 to the original value.

According to the configuration, it is possible to avoid a situation where noises due to the operation of the third switch 11 are overlapped with the evoked potential. Therefore, the accuracy of measurement of the evoked potential can be further improved.

In the embodiment, as illustrated in FIG. 2A, the capacitor C constituting a part of the high-pass filter 7 is included in the feedback loop for the amplifier A1 constituting a part of the second amplifier circuit 8.

According to the configuration, the operation of stopping the charging/discharging of the capacitor C as well as the operation of decreasing the gain G of the second amplifier circuit 8 can be performed by the common second switch 10. In other words, the second switch 10 may independently include a switch element which performs the operation of stopping the charging/discharging of the capacitor C as well as another switch element which performs the operation of decreasing the gain G of the second amplifier circuit 8.

In the embodiment, the first switch 6 is a negative logic photo-MOS relay. The first switch 6 which is disposed on the side close to the living body 100 is required to have resistance to static electricity. A photo-MOS relay can satisfy the requirement. Moreover, since the first and second lead electrodes 3, 4 are electrically connected to the first amplifier circuit 5 in the normal state, the power consumption can be reduced in the case where a negative logic device is used.

In the embodiment, the second and third switches 10, 11 are positive logic SPST (Single-Pole Single-Throw) analog switches. The switches are required to have a high response speed. An SPST switch can satisfy the requirement. Moreover, since the second and third switches 10, 11 are opened in the normal state, the power consumption can be reduced in the case where positive logic devices are used.

The above-described embodiment is a mere example for facilitating understanding of the disclosed concept. The configuration of the embodiment may be adequately changed or improved without departing from the disclosed concept.

The evoked potential illustrated in FIG. 3B is an example of the case where all of the first, second, and third switches 6, 10, 11 operate. However, in the case where it is required to attain only the effect that a fast artifact tail is suppressed by reducing the currents flowing into the first and second lead electrodes 3, 4, the evoked potential measuring apparatus 1 may be configured so as not to comprise the second and third switches 10, 11.

In the above embodiment, the pair of lead electrodes (the first and second lead electrodes 3, 4) is attached to the living body 100. However, it is possible to employ a configuration wherein two or more pairs of lead electrodes are attached to the living body 100, so that response waveforms based on differences of evoked potentials which are acquired from the respective pairs of lead electrodes are displayed on the displaying section 9. In this case, the aforementioned effect of suppressing a fast artifact tail is attained when the above-described operation is performed with respect to the first switch 6 associated with a pair of lead electrodes which is not subjected to the displaying operation of the displaying section 9.

Alternatively, in the case where it is required to attain only the effect that a slow artifact tail is suppressed by stopping the charging/discharging of the capacitor C during the application of stimulation, the evoked potential measuring apparatus 1 may be configured so as not to comprise the first and third switches 6, 11. In this case, the second switch 10 may have only the function of stopping the charging/discharging of the capacitor C at least while the stimulation is applied.

Alternatively, in the case where it is required to attain only the effect that an artifact tail are suppressed by decreasing the gain G of the second amplifier circuit 8 while the electrical connections between the first and second lead electrodes 3, 4 and the first amplifier circuit 5 is canceled, the evoked potential measuring apparatus 1 may be configured so as not to comprise the third switch 11. In this case, the second switch 10 may have only the function of decreasing the gain G of the second amplifier circuit 8 at least while the electrical connections between the first and second lead electrodes 3, 4 and the first amplifier circuit 5 is canceled.

Alternatively, in the case where it is required to attain only the effect that a fast artifact tail is suppressed by raising the cutoff frequency $f_c$ of the high-pass filter 7 after the application of stimulation, the evoked potential measuring apparatus 1 may be configured so as not to comprise the first and second switches 6, 10.

In the above embodiment, the first switch 6 is a negative logic photo-MOS relay. However, any adequate switch element may be employed as the first switch 6 as long as the switch element can selectively establish or cancel the electrical connections between the first and second lead electrodes 3, 4 and the first amplifier circuit 5. A positive logic photo-MOS relay, a mechanical relay, and an analog switch may be exemplified as such a switch.

In the above embodiment, the second switch 10 is a positive logic SPST analog switch. However, any adequate switch may be employed as the second switch 10 as long as the switch can perform the opening/closing operations for stopping the charging/discharging of the capacitor C as well as for decreasing the gain of the second amplifier circuit 8. A negative logic SPST analog switch, a mechanical relay, and a photo-MOS relay may be exemplified as such a switch.

In the above embodiment, the third switch 11 is a positive logic SPST analog switch. However, any adequate switch may be employed as the third switch 11 as long as the switch can perform the opening/closing operations for raising the cutoff frequency $f_c$ of the high-pass filter 7. A negative SPST analog switch, a mechanical relay, and a photo-MOS relay may be exemplified as such a switch element.

The configurations which have been described heretofore relate to a biopotential measuring apparatus for measuring the potential of nerve or muscle. However, the above-described configurations can also be applied to other biopotential measuring apparatuses such as an electrocardiogram examination.

The present application is based on Japanese Patent Application No. 2016-120196 filed on Jun. 16, 2016, the entire contents of which are hereby incorporated by reference.

The invention claimed is:

1. A biopotential measuring apparatus comprising:
    a stimulating electrode configured to apply a stimulation to a living body;
    a first lead electrode adapted to be attached on the living body;
    a second lead electrode adapted to be attached on the living body;
    a first amplifier circuit configured to amplify potential difference that is evoked between the first lead electrode and the second lead electrode due to the stimulation;
    a first switch configured to cancel electrical connection between the first amplifier circuit and each of the first lead electrode and the second lead electrode at least while the stimulation is applied;

a high-pass filter including a capacitor and a resistor, and configured to filter a frequency component of an output from the first amplifier circuit that is no less than a predetermined value;

a second amplifier circuit configured to amplify the output from the first amplifier circuit;

a second switch configured to stop charging/discharging of the capacitor and to decrease a gain of the second amplifier circuit at least while the first switch cancels the electrical connection between the first amplifier circuit and each of the first lead electrode and the second lead electrode; and a third switch connected in parallel to both terminals of the resistor, configured to increase a cutoff frequency of the high-pass filter by being closed after the stimulation is applied.

2. The biopotential measuring apparatus according to claim 1, wherein the third switch is configured to increase the cutoff frequency after the first switch restores the electrical connection between the first amplifier circuit and each of the first lead electrode and the second lead electrode.

3. The biopotential measuring apparatus according to claim 1 or 2, wherein the third switch is configured to increase the cutoff frequency when or after the second switch cancels stopping of the charging/discharging of the capacitor and decreasing of the gain of the second amplifier circuit.

4. The biopotential measuring apparatus according to claim 1, wherein the third switch is configured to restore the cutoff frequency before a response waveform, that is evoked between the first lead electrode and the second lead electrode due to the stimulation, appears.

5. The biopotential measuring apparatus according to claim 1, wherein the capacitor is included in a feedback loop of the second amplifier circuit.

6. The biopotential measuring apparatus according to claim 1, wherein the first switch is a negative logic photo-MOS relay, and the second switch is a positive logic SP ST analog switch.

7. The biopotential measuring apparatus according to claim 1, wherein the third switch is a positive logic SPST analog switch.

8. A biopotential measuring apparatus comprising:
a stimulating electrode configured to apply a stimulation to a living body;

a first lead electrode adapted to be attached on the living body;

a second lead electrode adapted to be attached on the living body;

an amplifier circuit configured to amplify potential difference that is evoked between the first lead electrode and the second lead electrode due to the stimulation;

a high-pass filter configured to filter a frequency component of an output from the amplifier circuit that is no less than a predetermined value, the high-pass filter including a capacitor and a resistor; and a switch connected in parallel to both terminals of the resistor, wherein the switch is configured to increase a cutoff frequency of the high-pass filter by being closed after the stimulation is applied.

9. The biopotential measuring apparatus of claim 8, further comprising:

a first switch configured to cancel an electrical connection between the amplifier circuit and each of the first lead electrode and the second lead electrode at least while the stimulation is applied.

10. The biopotential measuring apparatus of claim 9, comprising:

a second amplifier circuit configured to amplify the output from the amplifier circuit; and a second switch configured to stop charging/discharging of the capacitor and to decrease a gain of the second amplifier circuit at least while the first switch cancels the electrical connection between the first amplifier circuit and each of the first lead electrode and the second lead electrode.

\* \* \* \* \*

UNITED STATES PATENT AND TRADEMARK OFFICE
CERTIFICATE OF CORRECTION

PATENT NO. : 11,122,985 B2
APPLICATION NO. : 16/308311
DATED : September 21, 2021
INVENTOR(S) : Sato et al.

It is certified that error appears in the above-identified patent and that said Letters Patent is hereby corrected as shown below:

In the Claims

Column 11, Line 38, "positive logic SP ST" should read -- positive logic SPST --

Signed and Sealed this
Nineteenth Day of July, 2022

Katherine Kelly Vidal
*Director of the United States Patent and Trademark Office*